United States Patent [19]
Yashiro et al.

[11] Patent Number: 5,932,721
[45] Date of Patent: Aug. 3, 1999

[54] PHTHALOCYANINE COMPOUNDS

[75] Inventors: Toru Yashiro, Yokosuka; Masatoshi Taniguchi; Toshiro Narizuka, both of Kyoto, all of Japan

[73] Assignee: Ricoh Company, Ltd., Tokyo, Japan

[21] Appl. No.: 08/823,623

[22] Filed: Mar. 25, 1997

[30] Foreign Application Priority Data

Aug. 5, 1996 [JP] Japan ................... 8-221699

[51] Int. Cl.$^6$ .......................... C07D 487/22; C09B 47/04
[52] U.S. Cl. .......................... 540/139; 540/122; 540/140
[58] Field of Search ..................... 540/122, 139

[56] References Cited

U.S. PATENT DOCUMENTS

| | | | |
|---|---|---|---|
| 4,814,256 | 3/1989 | Aldag et al. | 430/270 |
| 5,169,745 | 12/1992 | Yashiro et al. | 428/64 |
| 5,238,722 | 8/1993 | Yashiro et al. | 428/64 |
| 5,242,730 | 9/1993 | Yashiro et al. | 428/64 |
| 5,252,372 | 10/1993 | Yashiro et al. | 428/64 |
| 5,580,696 | 12/1996 | Yashiro | 430/270.17 |

FOREIGN PATENT DOCUMENTS

| | | |
|---|---|---|
| 272565 | 6/1988 | European Pat. Off. |
| 337209 | 3/1989 | European Pat. Off. |
| 373643 | 12/1989 | European Pat. Off. |
| 491951 | 3/1991 | European Pat. Off. |
| 513370 | 10/1991 | European Pat. Off. |
| 492508 | 7/1992 | European Pat. Off. |
| 703280 | 9/1995 | European Pat. Off. |
| 703281 | 9/1995 | European Pat. Off. |
| WO9526381 | 10/1995 | WIPO. |

OTHER PUBLICATIONS

Chemical Abstracts, vol. 122, No. 16, Apr. 17, 1995 Kobayasi, H. et al. Active transport of alkali metal ions under two–phase . . .

Chemical Abstracts, vol. 124, No. 12. Sakamoto, M. "Phthalocyanine recording material and rewritable compact disk", 1996.

Chemical Abstracts, vol. 124, No. 18. Kimura, M. et al. "Soluble phthalocyanine and its mitro and amino derivatives and polymers . . . ".

Chemical Abstracts, vol. 111 No. 6, Aug. 7, 1989 Columbus, Ohio Miyoshi, H. et al. Phthalocyanine, for optical recording media . . .

*Primary Examiner*—John M. Ford
*Assistant Examiner*—Pavanaram K Sripada
*Attorney, Agent, or Firm*—Cooper & Dunham LLP

[57] ABSTRACT

A phthalocyanine compound of formula (1):

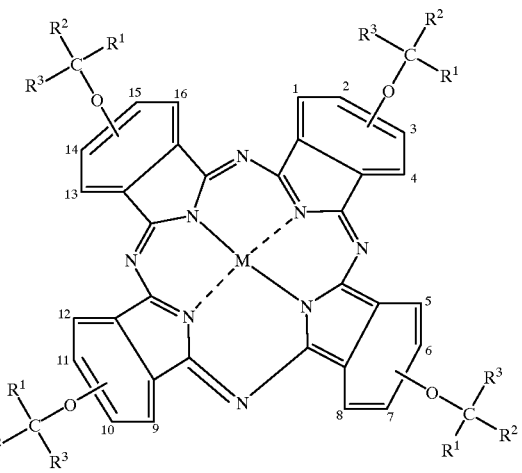

wherein FIGS. 1 to 16 around the phthalocyanine skeleton indicate the positions of carbon atoms, an oxygen atom is bonded to the carbon atom with position 1 or 4, to the carbon with position 5 or 8, to the carbon atom with position 9 or 12, and to the carbon atom with position 13 or 16, $R^1$ is a fluorine-atom substituted alkyl group, $R^2$ is an unsubstituted phenyl group or an alkyl-group-substituted phenyl group, $R^3$ is an unsubstituted alkyl group, a fluorine-atom substituted alkyl group or a hydrogen atom, and M represents VO or TiO.

5 Claims, No Drawings

PHTHALOCYANINE COMPOUNDS

BACKGROUND OF THE INVENTION

1. Field of the Invention

The present invention relates to novel phthalocyanine compounds which can be employed as a dye for optical recording, a dye for color filter, and a material for use in photoelectric conversion device, electrophotographic photoconductor, organic semiconductor device, catalysts, gas sensor, and color filter.

2. Discussion of Background

Phathalocyanine compounds attract attention not only as conventionally employed pigments, but also as dyes for optical recording media, dyes for color filter, and materials for use in photoelectric conversion device, electrophotographic photoconductor, organic semiconductor device, catalysts, gas sensor, and color filter.

However, unsubstituted phthalocyanine compounds are slightly soluble or insoluble in most solvents and therefore considerably lack workability.

For instance, when a thin film of a phthalocyanine compound is formed in order to use the phthalocyanine compound for the above-mentioned applications, vacuum deposition or ultra fine particle dispersion method is employed. In either method, the productivity is extremely low. Thus, the slight solubility or insolubility in solvents of phthalocyanine compounds is a great obstacle to the mass production of the above-mentioned media and devices.

In particular, when a phthalocyanine compound film prepared by vacuum deposition is used as a recording layer for an optical disk, it is necessary to perform crystal transformation of the recording layer into such a crystal form that is suitable for obtaining the recording characteristics required for the optical disk. This crystal transformation has to be conducted by heating the vacuum deposited phthalocyanine recording layer or exposing the vacuum deposited phthalocyanine recording layer to the vapor of an organic solvent for an extended period of time and the productivity of this method is significantly poor and therefore not used in practice for the production of optical disks.

With respect to optical disks, in particular, with compact disks, write once read many type compact disks have recently been actively developed. As organic dyes used as the materials for such write one read many type compact disks, cyanine dyes have been mainly used. Cyanine dyes are excellent in that they have large adsorptively coefficients, but have the shortcoming of not being heat resistant. In order to eliminate this shortcoming, it has been proposed to add a stabilizer such as a singlet oxygen quencher to the cyanine dyes. However, the addition of such a stabilizer is not sufficiently effective.

In sharp contrast to this, phthalocyanine dyes are comparable to the cyanine dyes and therefore the cyanine dyes can be replaced by phthalocyanine dyes with respect to the light absorption wavelength, and phthalocyanine dyes also have high light stability and are therefore expected to find many applications in the field of recording materials. However, for such applications, the problem of phthalocyanine dyes that the solubilities thereof in organic solvents are extremely low has to be solved.

In order to solve this problem, it has been proposed to introduce some substituents into a phthalocyanine compound to improve the solubility thereof in organic solvents and use the phthalocyanine compound in the form of a coating liquid by dissolving the phthalocyanine compound in a solvent. For instance, in Japanese Laid-Open Patent Applications 1-180865, 2-265788 and 63-31288, there are disclosed phthalocyanine compounds with improved solubilities in organic solvents such as hydrocarbons with the introduction of an alkyl group, an alkoxyl group, or an alkylthio group in each benzene ring of phthalocyanine compounds.

Furthermore, it has been tried to introduce various functional groups such as ester group and polyether group into each benzene group of phthalocyanine dye compounds to increase the solubilities of phthalocyanine dye compounds in organic solvents.

However, when phthalocyanine compounds are used in a light absorption layer for an optical information recording medium, the phthalcyanine dye compounds have not only the problems of extremely low solubilities in organic solvents and poor workability, but also the problems that the absorptivity coefficients thereof on a longer wavelength side are lowered by the association of the molecules of the phthalocyanine dye compound in a superimposed manner when a film thereof is prepared because of the exceedingly high flatness of each phthalocyanine dye compound molecule, and that when used in write one read many type compact disks, with application of laser beams thereto, the recording sensitivity is not high due to the exceedingly high thermal stability of the phthalocyanine dye compounds.

The phthalocyanine dye compounds disclosed in the above-mentioned Japanese Patent Applications are improved with respect to the film formation properties, but the optical characteristics and thermal characteristics thereof are unsatisfactory and the above-mentioned problems have not yet been solved.

SUMMARY OF THE INVENTION

It is therefore an object of the present invention to provide a phthalocyanine compound which is improved not only with respect to the solubility in organic solvents, but also with respect to the optical characteristics and thermal characteristics when formed into a film, and therefore, when used in write once read many type compact disks, is capable of having the compact disks exhibit high recording and reproduction performance.

This object of the present invention can be achieved by a phthalocyanine compound of formula (I):

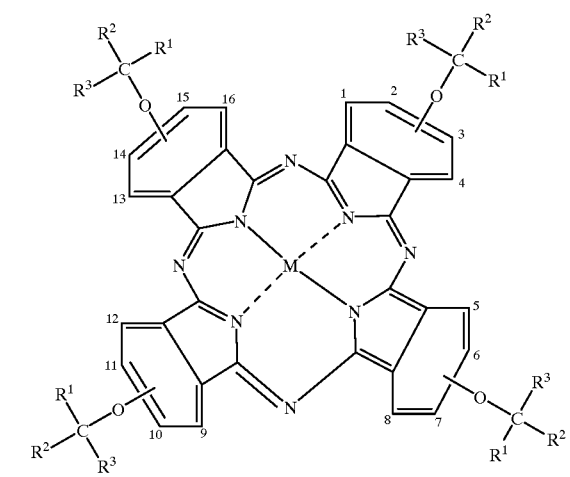

wherein numbers 1 to 16 around the phthalocyanine skeleton indicate the positions of carbon atoms in each benzene ring thereof, an oxygen atom is bonded to the carbon atom with position 1 or 4, to the carbon with position 5 or 8, to the carbon atom with position 9 or 12, and to the carbon atom with position 13 or 16, $R^1$ is a fluorine-atom substituted alkyl group, $R^2$ is an unsubstituted phenyl group or an alkyl-group-substituted phenyl group, $R^3$ is an unsubstituted alkyl group, a fluorine-atom substituted alkyl group or a hydrogen atom, and M represents VO or TiO.

DESCRIPTION OF THE PREFERRED EMBODIMENTS

The phthalocyanine compound of the present invention is represented by formula (I):

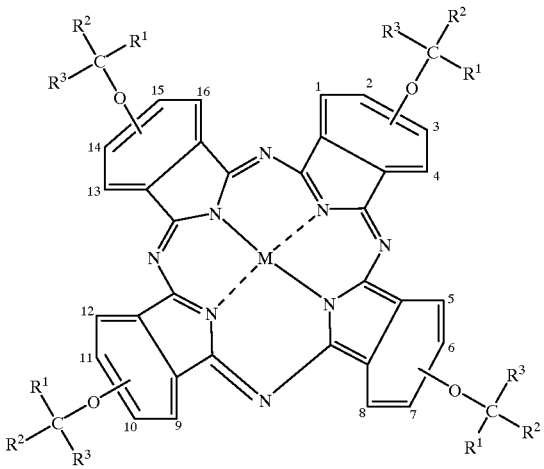

wherein numbers 1 to 16 around the phthalocyanine skeleton indicate the positions of carbon atoms in each benzene ring thereof, an oxygen atom is bonded to the carbon atom with position 1 or 4, to the carbon with position 5 or 8, to the carbon atom with position 9 or 12, and to the carbon atom with position 13 or 16, $R^1$ is a fluorine-atom substituted alkyl group, $R^2$ is an unsubstituted phenyl group or an alkyl-group-substituted phenyl group, $R^3$ is an unsubstituted alkyl group, a fluorine-atom substituted alkyl group or a hydrogen atom, and M represents VO or TiO.

In the phthalocyanine compound of the above formula (I), specific examples of the fluorine-atom substituted alkyl group represented by $R^1$ are trifluoromethyl group, pentafluroethyl group, heptafluoro-n-propyl group, heptafluoro-iso-propyl group, and nonafluoro-n-butyl group.

Specific examples of the unsubstituted phenyl group or alkyl-group-substituted phenyl group represented by $R^2$ are phenyl group, 2-methylphenyl group, 4-methyl-phenyl group, 2,5-dimethylphenyl group, 2,4-dimethyl-phenyl group, 2,4,6-trimethylphenyl group, 2,5-di-iso-propylphenyl group and 2,5-di-tert-butylphenyl group.

Specific examples of the unsubstituted alkyl group represented by $R^3$ are methyl group, ethyl group, n-propyl group, iso-propyl group, n-butyl group, iso-butyl group, sec-butyl group, tert-butyl group, and straight chain or branched pentyl group, hexyl group, heptyl group and octyl group.

Specific examples of the alkyl moiety of the fluorine-atom substituted alkyl group represented by $R^3$ are the same as the above-mentioned specific examples of the unsubstituted alkyl group represented by $R^3$.

The phthalocyanine compound of formula (I) of the present invention can be synthesized by allowing a phthalonitrile derivative, which is synthesized in accordance with a procedure as will be explained later, to react with a necessary metal salt in the presence of a strong organic base such as 1,8-diazabicyclo[5.4.0]-7-undecene (DBU) or 1,5-diaza-bicyclo[4.3.0]-5-nonene (DBN), in an alcohol solvent such as methanol, ethanol or n-pentanol.

The thus obtained phthalocyanine compound is highly soluble in various organic solvents such as hydrocarbon solvents, ether solvents, alcohol solvents, and aromatic solvents, assuming a blue green or green color when dissolved in these solvents.

By spin coating a solution of the phthalocyanine compound in any of the above solvents, for instance, on a polycarbonate substrate, a uniform thin layer of the phthalocyanine compound can be formed.

The thus prepared thin layer of the phthalocyanine compound does not exhibit a decreased absorptivity coefficient in a visible wavelength area, unlike thin layers of conventional phthalocyanine compounds, so that the thin layer of the phthalocyanine compound is suitable for use in an optical information recording medium.

In the phthalocyanine compound of the present invention, the phenyl group or fluorine-atom-substituted alkyl group is bulky, and the vanadyl group or titanyl group in the center of the molecule of the phthalocyanine compound enhances the non-flatness of the molecule of the phthalocyanine compound, so that the association of the molecules of the phthalocyanine compound, which causes a significant reduction in light absorption, is significantly hindered.

It is considered that the above-mentioned preferable absorption spectrum characteristics of the phthalocyanine compound of the present invention are available due to the above-mentioned hindering of the association of the molecules of the phthalocyanine compound.

Further, with respect to the thermal characteristics of the phthalocyanine compound, the moiety of the phenylmethyloxy group, which is contained in the phthalocyanine compound of the present invention, is generally considered to have an easily thermally decomposable structure. As a matter of fact, the phthalocyanine compound represented by formula (I) of the present invention is exothermically decomposed at temperatures in the range of 200° C. to 350° C., so that the phthalocyanine compound represented by formula (I) of the present invention is suitable as the material for write once read many type compact disks.

Furthermore, the fluorine atoms contained in the phthalocyanine compound of the present invention exhibit strong electron attractive properties, so that the fluorine atoms work in competition with electron-donating substituents such as alkyl group with respect to the light absorption wavelength, thermal stability and light stability.

The overall characteristics of the molecule of the phthalocyanine compound of the present invention can be controlled with the balance between the above-mentioned characteristic atoms and substituents being taken into consideration, and can also be suitably adjusted for use in the write once read many type compact disks which require delicate adjustments to the characteristics thereof.

Thus, the phthalocyanine compound of the present invention has high adaptability as the material for the write once read many compact disks.

The phthalonitrile derivative with a flourine-containing substituent, which is necessary for the synthesis of the phthalocyanine compound of the present invention, can be prepared by allowing a fluorine-containing benzyl alcohol derivative, which can be synthesized by any of the following methods (a), (b) and (c), to react with 3-nitrophthalonitrile:

(a) a benzene derivative is allowed to react with a fluorine-containing carboxylic anhydride or a fluroine-containing halogenated carboxylic acid by Friedel-Crafts reaction to prepare a fluorine-containing acetophenone derivative, and the thus prepared fluorine-containing acetophenone derivative is reduced.

(b) a benzene derivative and a fluorine-containing acetone derivative are subjected to Friedel-Crafts reaction.

(c) a halogenated benzoyl derivative is allowed to react with a fluorine-containing unsaturated hydrocarbon in the present of a fluoride ion to prepare a fluorine-containing acetophenone derivative, and the thus prepared fluorine-containing acetophenone derivative is reduced.

Other features of this invention will become apparent in the course of the following description of exemplary embodiments, which are given for illustration of the invention and are not intended to be limiting thereof.

EXAMPLE 1

[Synthesis of Phthalocyanine Compound No. 1 in TABLE 1]

Step (1—1) (Synthesis of benzyl alcohol derivative of formula (1-2))

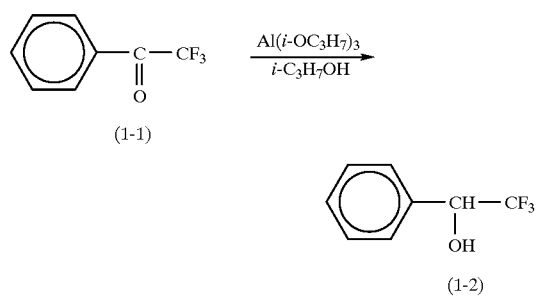

5.0 g of 2,2,2-trifluoroacetophenone of formula (1—1), 11.8 g of aluminum triisopropoxide, and 100 ml of isopropyl alcohol were placed in a flask equipped with a reflux condenser. This reaction mixture was heated with stirring to a refluxing temperature thereof and refluxed with stirring for 1 hour and 30 minutes.

This reaction mixture was then allowed to stand at room temperature and cooled to room temperature. The reaction mixture was then poured into 1000 ml of iced water, and the pH of the mixture was adjusted to 3 with the addition of a 20% aqueous solution of HCl thereto.

The above reaction mixture was extracted with 200 ml of toluene. The toluene extract layer was separated from the mixture and dried over magnesium sulfate. Toluene was distilled away from the toluene extract layer, whereby a benzyl alcohol of formula (1-2) was obtained as the residue in a yield of 5.1 g.

The analysis data of the thus obtained benzyl alcohol of formula (1-2) was as follows:

Mass spectrum: 175 (M$^+$)

IR spectrum: 3500 cm$^{-1}$ (vOH) 1120 to 1170 cm$^{-1}$ (vCF)

Step (1-2) (Synthesis of phthalonitrile derivative of formula (1-4))

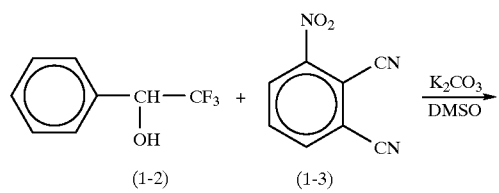

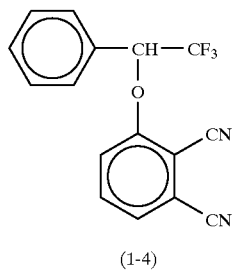

5.0 g of the benzyl alcohol derivative of formula (1-2) obtained in the above Step (1—1), 7.9 g of anhydrous potassium carbonate, 30 ml of dimethyl sulfoxide, and 4.5 g of 3-nitrophthalonitrile of formula (1-3) were placed in a flask.

This reaction mixture was stirred in a stream of nitrogen at 70° C. for 4 hours and then poured into 1000 ml of water. Crystals which separated out in the mixture were filtered off and dried, whereby a phthalonitrile derivative of formula (1-4) was obtained in a yield of 6 g.

The analysis data of the thus obtained phthalonitrile derivative of formula (1-4) was as follows:

Mass spectrum: 302 (M$^+$)

IR spectrum (KBr): 2230 cm$^{-1}$(vCN), 1140 to 1180 cm$^{-1}$(vCF)

Melting point: 165 to 167° C.

$^1$-NMR(CLCl$_3$): δ(ppm from TMS) 5.6 (1H, q), 7.1 (1H, d), 7.4–7.6 (7H, m)

Step (1-3) (Cyclization reaction for synthesis of phthalocyanine compound No. 1)

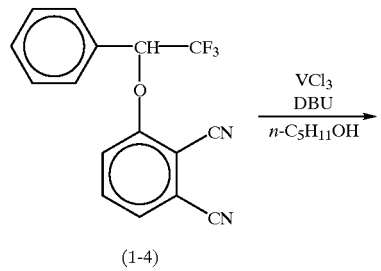

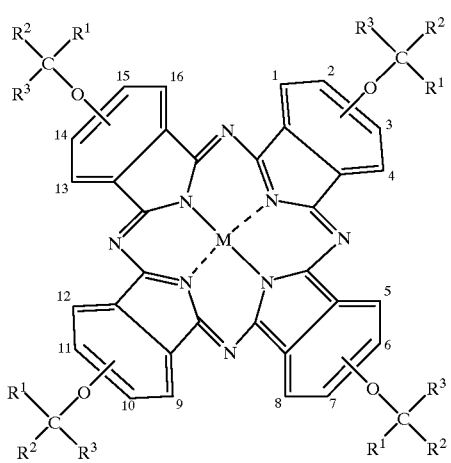

Phthalocyanine Compound No. 1

Phthalocyanine compound No. 1 is a phthalocyanine compound of formula (I) in which —O—CR$^1$R$^2$R$^3$ is

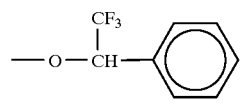

5 g of the phthalonitrile derivative of formula (1-4) prepared in the above Step (2), 3.8 g of 1,8-diazabicyclo[5.4.0]-7-undecene (hereinafter referred to as DBU), 40 ml of n-pentanol, and 0.87 g of vanadium trichloride were placed in a flask.

This reaction mixture was stirred in a stream of nitrogen at 110° C. for 18 hours.

This reaction mixture was then poured into 500 ml of methanol. To this mixture, 500 ml of water was further added. Crystals which separated out in the mixture were filtered off and dried, whereby a crude product of a phthalocyanine compound No. 1 was obtained in a yield of 5.4 g.

This crude product was subjected to column chromatogrpahy (silica gel/toluene: ethyl acetate=20:1), whereby a purified phthalocyanine compound No. 1 was obtained in a yield of 1.4 g.

The analysis data of the thus obtained phthalocyanine compound No. 1 was as follows:
IR spectrum (KBr): 1140 to 1180 cm$^{-1}$(vCF)
Solubility in 1,2-dichloroethane: 2% at room temperature
Solubility in toluene: 2% at room temperature
DSC analysis: Exothermic peaks near 300° C. (Ti 293° C., Tp 310° C.)
TG analysis: Reduction in weight began to be observed near 250° C.

The result of the elemental analysis of the phthalocyanine compound No. 1 was as follows:

|  | % C, | % H | % N |
|---|---|---|---|
| Found | 61.02 | 2.94 | 8.63 |
| Calc. | 60.25 | 2.35 | 8.78 |
|  |  |  | ($C_{54}H_{38}N_8O_3F_{12}V$) |

EXAMPLE 2

[Synthesis of Phthalocyanine Compound No. 2 in TABLE 1]

Step (2-1) (Synthesis of acetophenone derivative of formula (2—2))

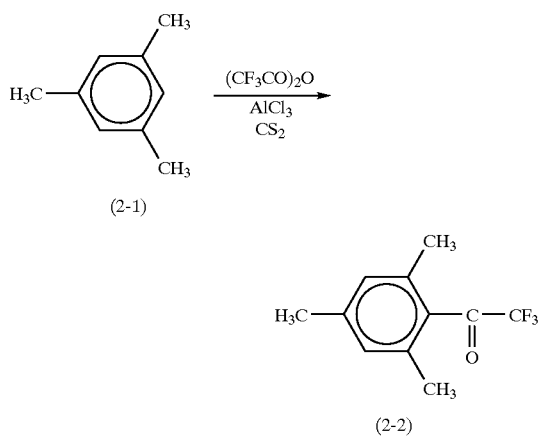

40 g of anhydrous aluminum chloride and 40 ml of carbon disulfide were placed in a flask equipped with a condenser. This reaction mixture was cooled with stirring to -10° C.

To this reaction mixture, 24 g of mesitylene of formula (2-1) was added dropwise over a period of 30 minutes. With the temperature of the reaction mixture being maintained at -10° C., 21 g of trifluoro acetic anhydride was added dropwise to the reaction mixture over a period of 40 minutes.

The reaction mixture was stirred at -12° C. to -8° C. for 2 hours and 30 minutes. The reaction mixture was then poured into 1000 ml of iced water. This mixture was extracted with 300 ml of toluene. The toluene extract layer was separated from the mixture and successively washed with 1000 ml of a 3% aqueous solution of sodium carbonate, and then with 1000 ml of water.

The thus washed toluene extract layer was dried over magnesium sulfate. Toluene and mesitylene were distilled away from the above extract layer, whereby an acetophenone derivative of formula (2—2) was obtained in the form of a pale yellow oil in a yield of 13 g.

The analysis data of the thus obtained acetophenone derivative of formula (2—2) was as follows:
Mass spectrum: 216 (M$^+$)
IR spectrum: 1740 cm$^{-1}$(vCO), 1150 to 1200 cm$^{-1}$(vCF)

Step (2—2) (Synthesis of benzyl alcohol derivative of formula (2-3))

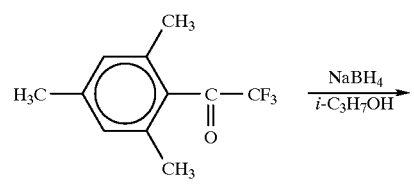

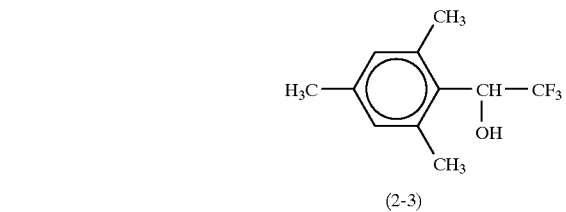

13 g of the acetophenone derivative of formula (2—2) prepared in the above Step (1—1) and 150 ml of isopropyl alcohol were placed in a flask.

To this reaction mixture, 7.5 g of sodium boron hydride was added, and the mixture was stirred at 40° C. for 2 hours. The reaction mixture was then cooled to room temperature and poured into 2000 ml of water.

The mixture was extracted with toluene. The toluene extract layer was washed with water and then dried over magnesium sulfate. Toluene was distilled away from the extract layer, and the extract layer was concentrated, whereby a benzyl alcohol derivative of formula (2-3) was obtained in the form of a pale oil in a yield of 12 g.

The analysis data of the thus obtained benzyl alcohol derivative of formula (2-3) was as follows:
Mass spectrum: 218 (M$^+$)
IR spectrum: No vCO absorption, 3500 cm$^{-1}$ (vOH), 1120 to 1170 cm$^{-1}$(vCF)

Step (2-3) (Synthesis of phthalonitrile derivative of formula (2-4))

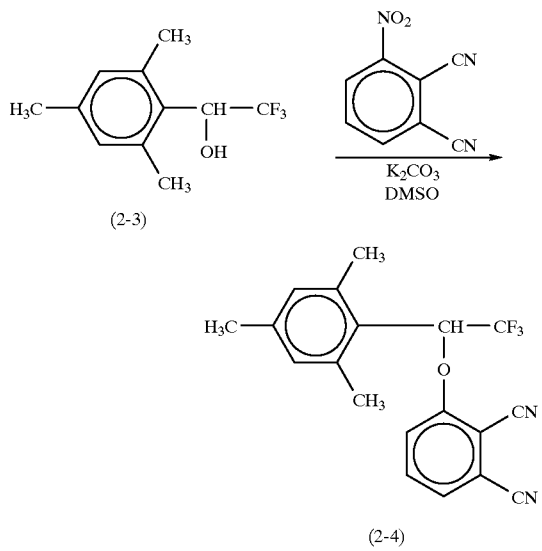

(2-3)

(2-4)

12 g of the benzyl alcohol derivative of formula (2-3) prepared in the above Step (2—2), 15 g of anhydrous potassium carbonate and 50 ml of dimethyl sulfoxide were placed in a flask.

To the above reaction mixture, a solution of 3.3 g of 3-nitrophthalonitrile in 50 ml of dimethyl sulfoxide was added dropwise with stirring at 60° C. over a period of 90 minutes.

This reaction mixture was stirred at 60° C. for 3 hours and then poured into 1000 ml of water. Crystals which separated out in the mixture were filtered off and dried, whereby a phthalonitrile derivative of formula (2-4) was obtained in the form of a pale yellow solid in a yield of 16 g.

The analysis data of the thus obtained phthalonitrile derivative of formula (2-4) was as follows:

Mass spectrum: 344 (M$^+$)

IR spectrum (KBr): 2240 cm$^{-1}$(vCN), 1140 to 1180 cm$^{-1}$(vCF)

Melting point: 170 to 175° C.

Step (2-4) (Cyclization Reaction for synthesis of phthalocyanine compound No. 2)

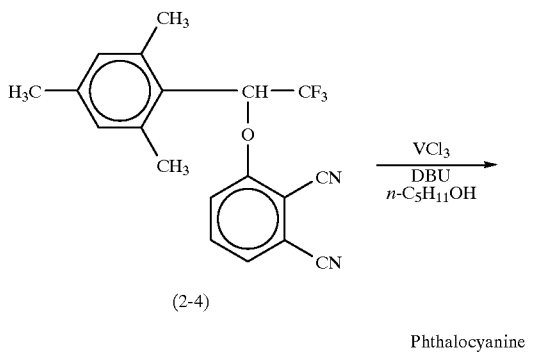

(2-4)

Phthalocyanine Compound No. 2

Phthalocyanine compound No. 2 is a phthalocyanine compound of formula (I) in which —O—CR$^1$R$^2$R$^3$ is

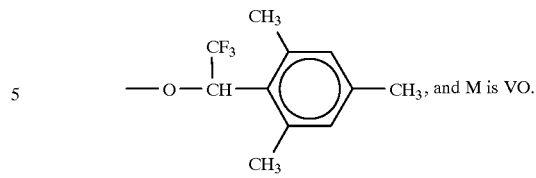

, and M is VO.

4 g of the phthalonitrile derivative of formula (2-4) prepared in the above Step (2-3), 2.7 g of DBU and 40 ml of n-pentanol were placed in a flask.

This reaction mixture was heated to 90° C. in a stream of nitrogen and 0.6 g of vanadium trichloride was added thereto. The reaction mixture was stirred at 100° C. for 6 hours.

With the heating of the reaction mixture being stopped, the reaction mixture was then poured into 300 ml of methanol. To this mixture, 100 ml of water was further added.

Crystals which separated out in the mixture were filtered off and dried, whereby a crude product of the phthalocyanine compound No. 2 was obtained in a yield of 3.3 g.

This crude product was subjected to column chromatography (silica gel/toluene:ethyl acetate=50:1), whereby a purified phthalocyanine compound No. 2 was obtained in a yield of 1.5 g.

The analysis data of the thus obtained phthalocyanine derivative was as follows:

IR spectrum (KBr): 1130 to 1180 cm$^{-1}$(vCF) 2920 cm$^{-1}$ (vCH) (methyl group)

Solubility in 1,2-dichloroethane: 2% at room temperature

Solubility in toluene: 2% at room temperature

Solubility in 2-ethoxyethanol: 1% at room temperature

DSC analysis: Exothermic peaks near 350° C. (Ti 344° C., Tp 355° C.)

TG analysis: Reduction in weight began to be observed near 250° C.

EXAMPLE 3

[Synthesis of Phthalocyanine Compound No. 3 in TABLE 1]

Step (3-1) (Synthesis of phthalonitrile derivative of formula (3-2)

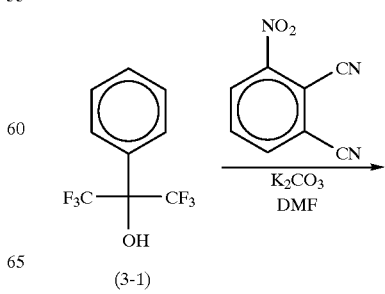

(3-1)

-continued

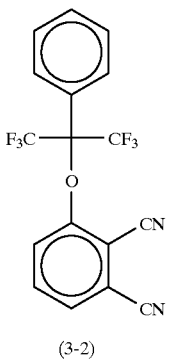

(3-2)

10 g of 1,1,1,3,3,3-hexafluoro-2-phenyl-2-propanol of formula (3-1), 16 g of anhydrous potassium carbonate and 25 ml of N,N-dimethylformamide were placed in a flask.

To the above reaction mixture, 4.8 g of 3-nitrophthalonitrile was added with stirring at 50 to 60° C. over a period of 40 minutes.

This reaction mixture was stirred at 70° C. for 6 hours and then poured into 600 ml of water. Crystals which separated out in the mixture were filtered off and dried, whereby a phthalonitrile derivative of formula (3-2) was obtained in the form of a solid in a yield of 5.2 g.

The analysis data of the thus obtained phthalonitrile derivative of formula (3-2) was as follows:

Melting point: 150 to 152° C.

Mass spectrum: 370 (M$^+$)

Step (3-2) (Cyclization reaction for synthesis of phthalocyanine compound No. 3)

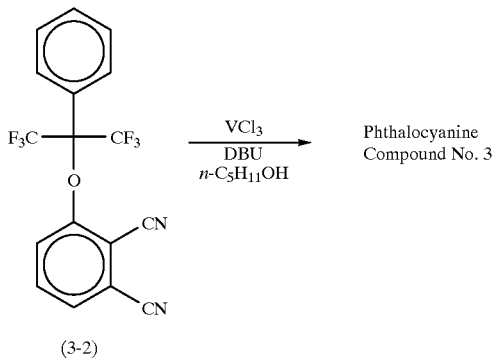

(3-2)

Phthalocyanine compound No. 3 is a phthalocyanine compound of formula (I) in which —O—CR$^1$R$^2$R$^3$ is

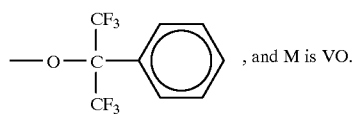

, and M is VO.

5.2 g of the phthalonitrile derivative of formula (3-2) prepared in the above Step (3-1), 5.1 g of DBU, 30 ml of n-pentanol and 0.73 g of vanadium trichloride were placed in a flask.

This reaction mixture was stirred in a stream of nitrogen at 90 to 95° C. for 8 hours, and poured into 600 ml of methanol. To this mixture, 80 ml of water was further added. A precipitate which separated out in the mixture was filtered off and dried, whereby a crude product of the phthalocyanine compound No. 3 was obtained in a yield of 2.4 g.

This crude product was subjected to column chromatogrpahy (silica gel/toluene:ethyl acetate=80:1), whereby a purified phthalocyanine compound No. 3 was obtained in a yield of 1.1 g.

The analysis data of the thus obtained phthalocyanine compound No. 3 was as follows:

Solubility in 1,2-dichloroethane: 2% at room temperature

DSC analysis: Exothermic peaks near 300° C. (Ti 296° C., Tp 311° C.)

TG analysis: Reduction in weight began to be observed near 250° C.

EXAMPLE 4

[Synthesis of Phthalocyanine Compound No. 4 in TABLE 1]

The procedure of the synthesis of the phthalocyanine compound No. 3 in Example 3 was repeated except that 0.73 g of vanadium trichloride employed in Step (3-2) in Example 3 was replaced by 0.5 g of titanium tetrachloride, whereby a phthalocyanine compound No. 4 shown in TABLE 1 was prepared and obtained in a yield of 0.8 g.

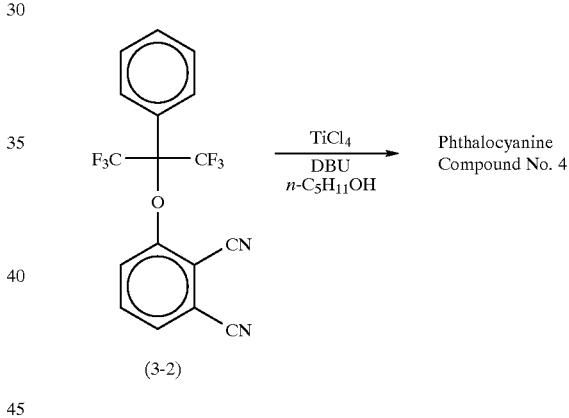

(3-2)

Phthalocyanine compound No. 4 is a phthalocyanine compound of formula (I) in which —O—CR$^1$R$^2$R$^3$ is

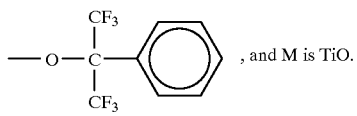

, and M is TiO.

The analysis data of the thus obtained phthalocyanine compound No. 4 was as follows:

Solubility in 1,2-dichloroethane:

2% at room temperature

DSC analysis:

Exothermic peaks near 300° C. (Ti 288° C., Tp 315° C.)

TG analysis:

Reduction in weight began to be observed near 250° C.

EXAMPLE 5

Synthesis of Phthalocyanine Compound No. 5 in TABLE 1

Step (5-1)
Synthesis of Acetophenone Derivative of Formula (5-2)

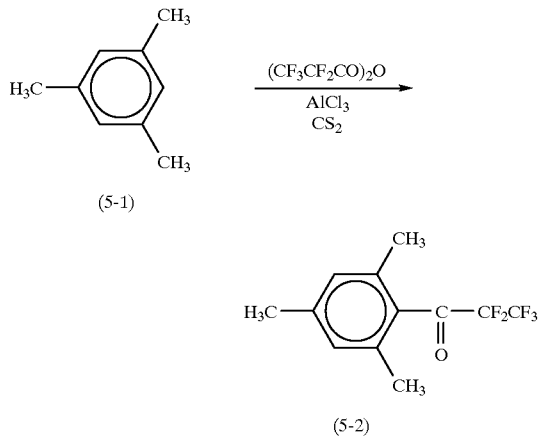

20 g of anhydrous aluminum chloride and 20 ml of carbon disulfide were placed in a flask equipped with a condenser. This reaction mixture was cooled with stirring to −15° C. To this reaction mixture, 12 g of mesitylene of formula (5-1) was added dropwise over a period of 30 minutes. With the temperature of the reaction mixture being maintained at −15° C. 15.5 g of pentafluoropropionic anhydride was added dropwise to the reaction mixture over a period of 30 minutes.

The reaction mixture was then stirred at −10° C. to −18° C. for 3 hours and 30 minutes.

The reaction mixture was then poured into 500 ml of iced water. This mixture was extracted with 200 ml of toluene. The toluene extract layer was separated from the mixture and successively washed with 500 ml of a 3% aqueous solution of sodium carbonate, and then with 1000 ml of water.

The thus washed extract layer was dried over magnesium sulfate. Toluene and mesitylene were distilled away from the above extract layer, whereby an acetophenone derivative of formula (5-2) was obtained in the form of a pale yellow oil in a yield of 5.8 g.

The analysis data of the thus obtained acetophenone derivative of formula (5-2) was as follows:

Mass spectrum:
266 (M$^+$)
IR spectrum:
1740 cm$^{-1}$ ($\upsilon$CO),
1140 to 1260 cm$^{-1}$ ($\upsilon$CF)

Step (5-2)
Synthesis of Benzyl Alcohol Derivative of Formula (5-3)

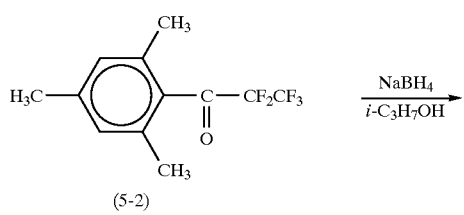

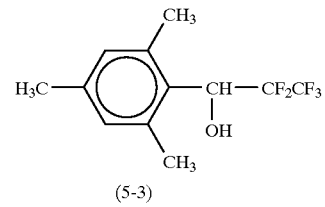

13 g of the acetophenone derivative of formula (5-2) prepared in the above Step (5-1) and 50 ml of isopropyl alcohol were placed in a flask.

To this reaction mixture, 2.6 g of sodium boron hydride was added at 40 to 50° C., and the mixture was stirred at 40° C. for 2 hours. This reaction mixture was then poured into 700 ml of water.

The mixture was extracted with toluene. The toluene extract layer was washed with water, then dried over anhydrous magnesium sulfate and concentrated, whereby a benzyl alcohol derivative of formula (5-3) was obtained in the form of a pale yellow oil in a yield of 5.4 g.

The analysis data of the thus obtained benzyl alcohol derivative of formula (5-3) was as follows:
Mass spectrum:
268 (M$^+$)
IR spectrum:
No $\upsilon$CO absorption,
3500 cm$^{-1}$ ($\upsilon$OH),
1130 to 1210 cm$^{-1}$ ($\upsilon$CF)

Step (5-3)
Synthesis of Phthalonitrile Derivative of Formula (5-4)

12 g of the benzyl alcohol derivative of formula (5-3) prepared in the above Step (5-2), 5.5 g of anhydrous potassium carbonate, 3.5 g of 3-nitrophthalonitrile and 50 ml of dimethyl sulfoxide were placed in a flask.

This reaction mixture was stirred at 60° C. for 2 hours. With the heating of the reaction mixture being stopped, the reaction mixture was poured into 500 ml of water. Crystals which separated out in the mixture were filtered off and dried, whereby a phthalonitrile derivative of formula (5-4) was obtained in the form of a white solid in a yield of 7.8 g.

The analysis data of the thus obtained phthalonitrile derivative of formula (5-4) was as follows:

Mass spectrum:
394 (M⁺)
IR spectrum (KBr):
2250 cm⁻¹ (υCN),
1140 to 1210 cm⁻¹ (υCF)
Melting point:
155 to 158° C.

Step (5-4)
Cyclization Reaction for Synthesis of Phthalocyanine Compound No. 5

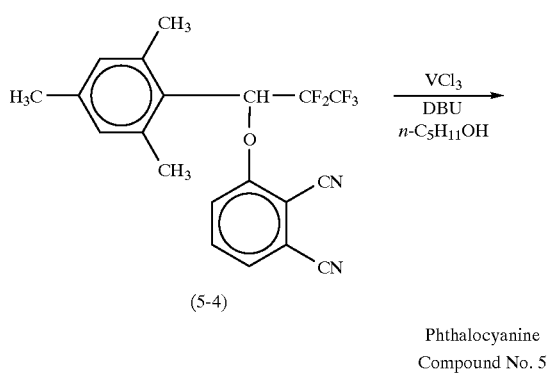

Phthalocyanine Compound No. 5

Phthalocyanine compound No. 5 is a phthalocyanine compound of formula (I) in which —O—CR¹R²R³ is

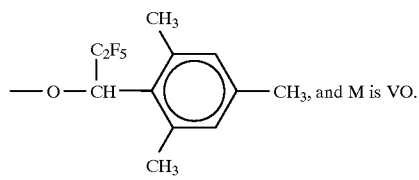

CH₃, and M is VO.

7.2 g of the phthalonitrile derivative of formula (5-4) prepared in the above Step (5-3), 3.5 g of DBU, 30 ml of n-pentanol and 1.6 g of vanadium trichloride were placed in a flask.

This reaction mixture was stirred in a stream of nitrogen at 100° C. for 20 hours.

With the hating of the reaction mixture being stopped, the reaction mixture was then poured into 400 ml of methanol, and insoluble components were removed from the mixture by filtration.

To the filtrate, 100 ml of water was added. Crystals which separated out in the mixture were filtered off and dried, whereby a crude product of the phthalocyanine compound No. 5 was obtained in a yield of 5.4 g.

This crude product of the phthalocyanine compound No. 5 was subjected to column chromatography (silica gel/toluene), whereby a purified phthalocyanine compound No. 5 was obtained in a yield of 0.4 g.

The analysis data of the thus obtained phthalocyanine compound was as follows:

Solubility in 1,2-dichloroethane:
5% at room temperature
DSC analysis:
Exothermic peaks near 250 to 350° C. (Ti 224° C., Tp 248° C., 294° C.)

TG analysis:
Reduction in weight began to be observed near 200° C.

EXAMPLE 6

Synthesis of Phthalocyanine Compound No. 6 in TABLE 1

Step (6-1)
Synthesis of Acetophenone Derivative of Formula (6-2)

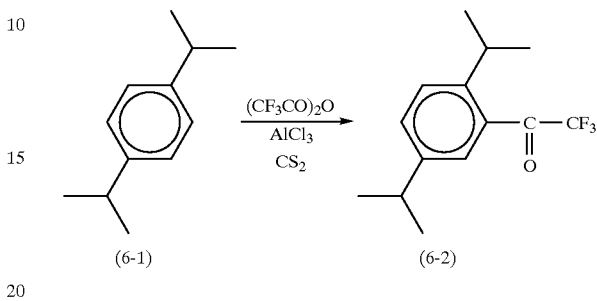

The procedure of the synthesis of the acetophenone derivative of formula (2-2) in Step (2-1) in Example 2 was repeated except that 24 g of mesitylene employed in Step (1-1) in Example 2 was replaced by 32 g of 2,5-diisopropylbenzene of formula (6-1), whereby an acetophenone derivative of formula (6-2) was obtained in a yield of 8.5 g.

The analysis data of the thus obtained acetophenone derivative of formula (6-2) was as follows:

Mass spectrum:
258 (M⁺)
IR spectrum:
1720 cm⁻¹ (υCO),
1150 to 1200 cm⁻¹ (υCF)

Step (6-2)
Synthesis of Benzyl Alcohol Derivative of Formula (6-3)

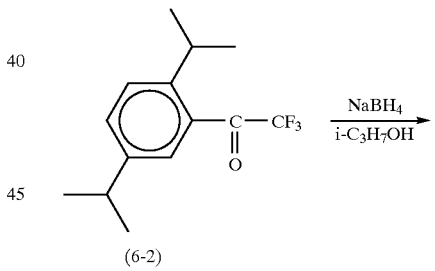

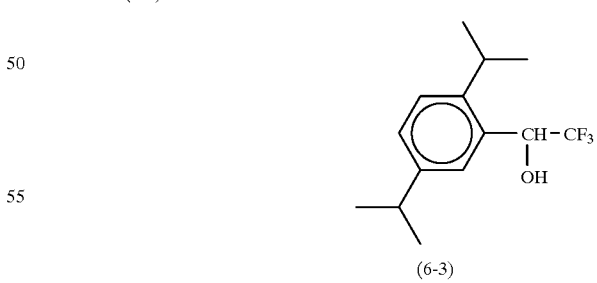

The procedure of the synthesis of the benzyl alcohol derivative of formula (2-3) in Step (2-2) in Example 2 was repeated except that 13 g of the acetophenone derivative for formula (2-2) employed in Step (2-2) in Example 2 was replaced by 4.0 g of the acetophenone derivative of formula (6-2) prepared in the above Step (6-1) for the reduction thereof, whereby a benzyl alcohol derivative of formula (6-3) was obtained in a yield of 2.2 g.

The analysis data of the thus obtained benzyl alcohol derivative of formula (6-3) was as follows:

Mass spectrum:

260 (M⁺)
IR spectrum:
3500 cm⁻¹ (υOH),
1130 to 1170 cm⁻¹ (υCF)

Step (6-3)

Synthesis of Phthalonitrile Derivative of Formula (6-4)

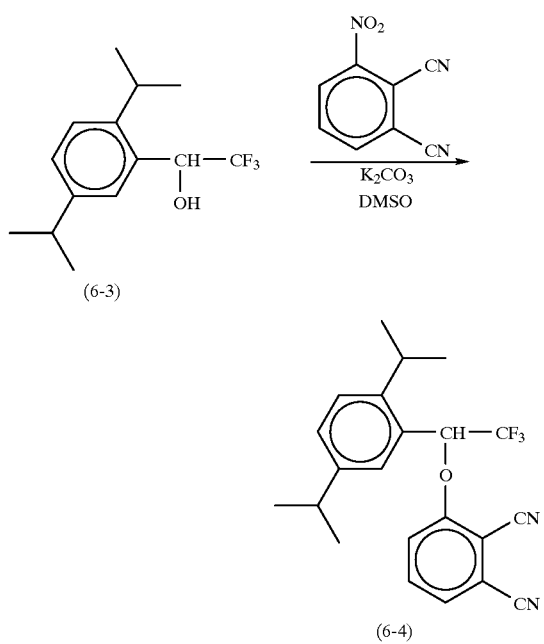

The procedure of synthesizing the phthalonitrile derivative of formula (2-4) in Step (2-3) in Example 2 was repeated except that the benzyl alcohol derivative of formula (2-3) in Step (2-3) in Example 2 was replaced by 2.2 g of the benzyl alcohol derivative of formula (6-3) obtained in the above Step (6-2), whereby a phthalonitrile derivative of formula (6-4) was obtained in the form of an oil in a yield of 2.4 g.

The analysis data of the thus obtained phthalonitrile derivative of formula (6-4) was as follows:

Mass spectrum:

386 (M⁺)
IR spectrum (KBr):
2240 cm⁻¹ (υCN),
1150 to 1180 cm⁻¹ (υCF)

Step (6-4)

Cyclization Reaction for Synthesis of Phthalocyanine Compound No. 6

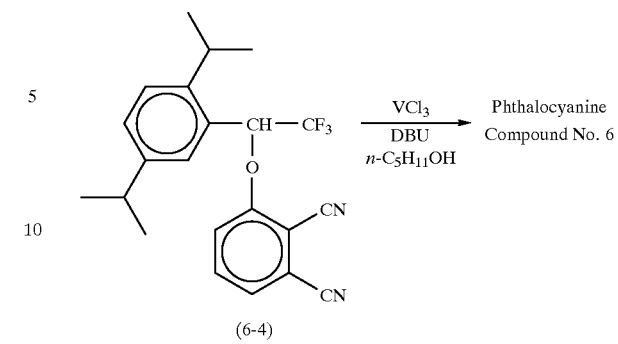

Phthalocyanine compound No. 6 is a phthalocyanine compound of formula (I) in which —O—CR¹R²R³ is

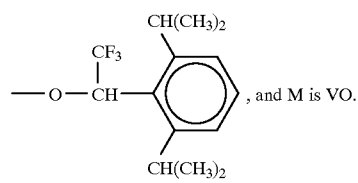

, and M is VO.

The procedure of synthesizing the phthalocyanine compound No. 2 in Step (2-4) in Example 2 was repeated except that 4 g of the phthalonitrile derivative of formula (2-4) employed in Step (2-4) in Example 2 was replaced by 2.4 g of the phthalonitrile derivative of formula (6-4) prepared in the above Step (6-3), whereby a crude phthalocyanine compound No. 6 was obtained in a yield of 1.0 g.

This crude product was subjected to column chromatography (silica gel/toluene), whereby a purified phthalocyanine compound No. 6 was obtained in a yield of 0.2 g.

The analysis data of the thus obtained phthalocyanine compound No. 6 was as follows:
Solubility in 1,2-dichloroethane:
5% at room temperature

EXAMPLE 7

Synthesis of Phthalocyanine Compound No. 7 in TABLE 1

Step (7-1)

Synthesis of Acetophenone Derivative of Formula (7-2)

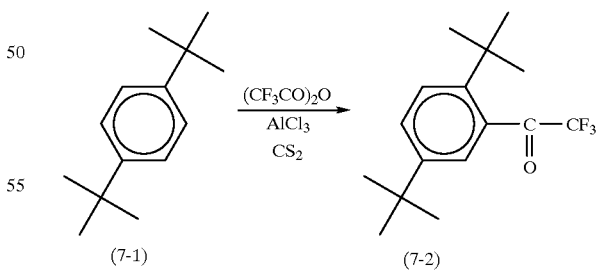

The procedure of the synthesis of the acetophenone derivative of formula (2-2) in Step (2-1) in Example 2 was repeated except that 24 g of mesitylene employed in Step (2-1) in Example 2 was replaced by 38 g of 2,5-di-tert-butylbenzene of formula (7-1), whereby an acetophenone derivative of formula (7-2) was obtained in a yield of 13 g.

The analysis data of the thus obtained acetophenone derivative of formula (7-2) was as follows:

Mass spectrum:

286 (M+)

IR spectrum:

1720 cm$^{-1}$ (υCO), 1150 to 1200 cm$^{-1}$ (υCF)

Step (7-2)

Synthesis of Benzyl Alcohol Derivative of Formula (7-3)

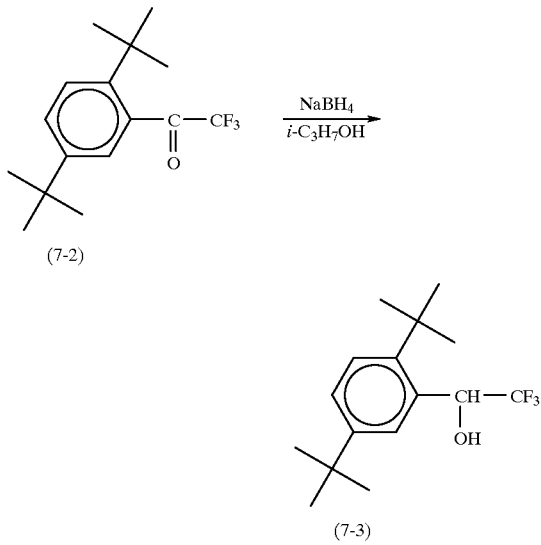

The procedure of the synthesis of the benzyl alcohol derivative of formula (2-3) in Step (2-2) in Example 2 was repeated except that 4.0 g of the acetophenone derivative for formula (2-2) employed in Step (2-2) in Example 2 was replaced by 13 g of the acetophenone derivative of formula (7-2) prepared in the above Step (7-1) for the reduction thereof, whereby a benzyl alcohol derivative of formula (7-3) was obtained in a yield of 7.3 g.

The analysis data of the thus obtained benzyl alcohol derivative of formula (7-3) was as follows:

Mass spectrum:

288 (M+)

IR spectrum:

3400 to 3550 cm$^{-1}$ (υOH), 1130 to 1170 cm$^{-1}$ (υCF)

Step (7-3)

Synthesis of Phthalonitrile Derivative of Formula (7-4)

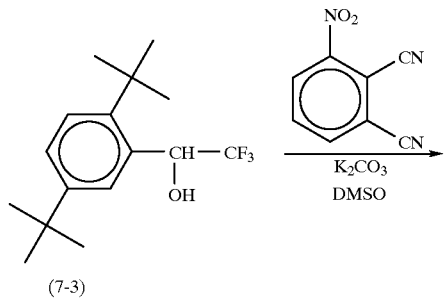

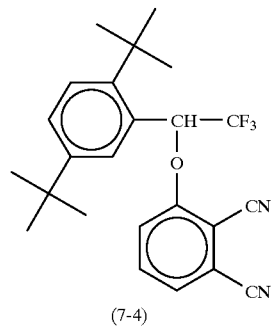

The procedure of synthesizing the phthalonitrile derivative of formula (2-4) in Step (2-3) in Example 2 was repeated except that the benzyl alcohol derivative of formula (2-3) employed in Step (2-3) in Example 2 was replaced by 7.3 g of the benzyl alcohol derivative of formula (7-3) prepared in the above Step (7-2), whereby a phthalonitrile derivative of formula (7-4) was obtained in a yield of 7.5 g.

The analysis data of the thus obtained phthalonitrile derivative of formula (7-4) was as follows:

Mass spectrum:

414 (M+)

IR spectrum (KBr):

2250 cm$^{-1}$ (υCN), 1150 to 1180 cm$^{-1}$ (υCF)

Step (7-4)

Cyclization Reaction for Synthesis of Phthalocyanine Compound No. 7

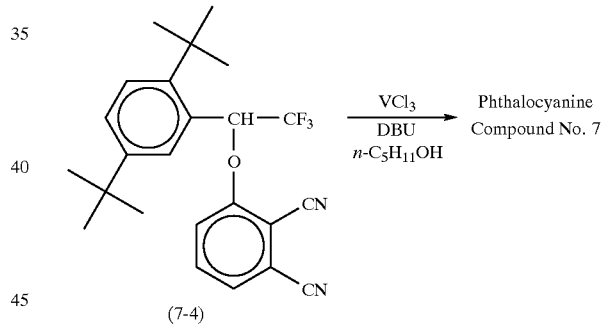

Phthalocyanine compound No. 7 is a phthalocyanine compound of formula (I) in which —O—CR$^1$R$^2$R$^3$ is

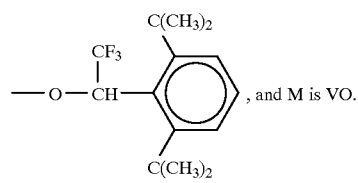

, and M is VO.

The procedure of synthesizing the phthalocyanine compound No. 2 in Step (2-4) in Example 2 was repeated except that the phthalonitrile derivative of formula (2-4) employed in Step (2-4) in Example 2 was replaced by 4.0 g of the phthalonitrile derivative of formula (7-4) prepared in the above Step (7-3), whereby a crude phthalocyanine compound No. 7 was obtained in a yield of 0.87 g.

This crude phthalocyanine compound No. 7 was subjected to column chromatography (silica gel/toluene), whereby a purified phthalocyanine compound No. 7 was obtained in a yield of 0.11 g.

The analysis data of the thus obtained phthalocyanine compound No. 7 was as follows:

Solubility in 1,2-dichloroethane:
5% at room temperature

EXAMPLE 8

Synthesis of Phthalocyanine Compound No. 8 in TABLE 1

Step (8-1)
Synthesis of Acetophenone Derivative of Formula (8-2)

<chemical structure>
Ph—C(=O)—Cl  →(CF$_3$CF=CF$_2$, KF, DMF)→  Ph—C(=O)—CF(CF$_3$)—CF$_3$
(8-1)                                         (8-2)
</chemical structure>

14 g of benzoyl chloride of formula (8-1), 50 ml of dimethylformamide and 23 g of pulverized potassium fluoride were placed in a reactor. This reaction mixture was cooled with stirring to −40° C.

To this reaction mixture, 0.22 moles of hexafluoropropene was added. With the reactor tightly sealed, the temperature of the reaction mixture was returned to room temperature.

The reactor was then placed in an autoclave, and the reaction mixture was heated to 120° C. with stirring, and the stirring of the reaction mixture was continued at 120° C. for 6 hours. The reaction mixture was then allowed to stand at room temperature to cool the reaction mixture to room temperature.

The reaction mixture was then poured into 1000 ml of water. This mixture was extracted with diethyl ether. The extract layer was separated from the mixture and successively washed with an aqueous solution of sodium hydrogencarbonate, and then with water.

The thus washed extract layer was dried over anhydrous magnesium sulfate. Diethyl ether was distilled away from the above extract layer, and the residue was subjected to vacuum distillation at 80 to 82° C./40 mmHg, whereby an acetophenone derivative of formula (8-2) was obtained in a yield of 15 g.

The analysis data of the thus obtained acetophenone derivative of formula (8-2) was as follows:

Mass spectrum:
274 (M$^+$)
IR spectrum (KBr):
1700 cm$^{-1}$ ($\upsilon$CO),
1140 to 1200 cm$^{-1}$ ($\upsilon$CF)

Step (8-2)
Synthesis of Benzyl Alcohol Derivative of Formula (8-3)

<chemical structure>
Ph—C(=O)—CF(CF$_3$)—CF$_3$  →(NaBH$_4$, i-C$_3$H$_7$OH)→
(8-2)
</chemical structure>

<chemical structure>
Ph—CH(OH)—CF(CF$_3$)—CF$_3$
(8-3)
</chemical structure>

15 g of the acetophenone derivative of formula (8-2) prepared in the above Step (8-1) and 150 ml of isopropyl alcohol were placed in a flask.

The reaction mixture was heated with stirring to 40° C. To this reaction mixture, 8.5 g of sodium boron hydride was added, and the mixture was stirred at 40° C. for 3 hours. The reaction mixture was then poured into 2000 ml of water.

The mixture was extracted with toluene. The toluene extract layer was washed with water and then dried over anhydrous magnesium sulfate. Toluene was distilled away from the extract layer, whereby a benzyl alcohol derivative of formula (8-3) was obtained in the form of an oil in a yield of 14 g.

The analysis data of the thus obtained benzyl alcohol derivative of formula (8-3) was as follows:

Mass spectrum:
276 (M$^+$)
IR spectrum:
3500 cm$^{-1}$ ($\upsilon$OH),
1120 to 1200 cm$^{-1}$ ($\upsilon$CF)

Step (8-3)
Synthesis of Phthalonitrile Derivative of Formula (8-4)

<chemical structure>
Ph—CH(OH)—CF(CF$_3$)—CF$_3$ + 3-nitrophthalonitrile  →(K$_2$CO$_3$, DMSO)→
(8-3)
</chemical structure>

<chemical structure>
Ph—CH(—O—Ar(CN)$_2$)—CF(CF$_3$)—CF$_3$
(8-4)
</chemical structure>

14 g of the benzyl alcohol derivative of formula (8-3) prepared in the above Step (8-2) and 17 g of anhydrous potassium carbonate and 40 ml of dimethyl sulfoxide were placed in a flask.

To the above reaction mixture, 7.3 g of 3-nitrophthalonitrile was added with stirring at 50 to 60° C. over a period of 90 minutes.

This reaction mixture was stirred at 60° C. for 5 hours and then poured into 1000 ml of water. The mixture was extracted with toluene. The toluene extract layer was washed with water and then dried over anhydrous magnesium sulfate. Toluene was distilled away from the extract layer, and the residue was concentrated, whereby a phthalonitrile derivative of formula (8-4) was obtained in a yield of 11 g.

The analysis data of the thus obtained phthalonitrile derivative of formula (8-4) was as follows:

Mass spectrum (KBr):

402 (M+)

IR spectrum:

2240 cm$^{-1}$ (υCN), 1140 to 1210 cm$^{-1}$ (υCF)

Step (8-4)

Cyclization Reaction for Synthesis of Phthalonitrile Compound No. 8

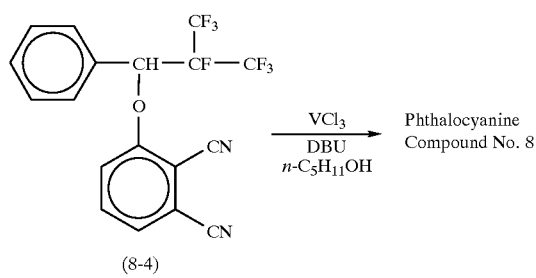

(8-4)

Phthalocyanine compound No. 8 is a phthalocyanine compound of formula (I) in which —O—CR$^1$R$^2$R$^3$ is

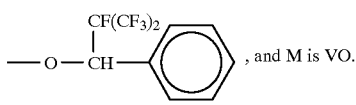, and M is VO.

4 g of the phthalonitrile derivative of formula (8-4) prepared in the above Step (8-3), 2.3 g of DBU and 40 ml of n-pentanol were placed in a flask.

This reaction mixture was heated to 90° C. in a stream of nitrogen and 0.52 g of vanadium trichloride was added thereto. The reaction mixture was stirred at 90 to 100° C. for 10 hours.

With the heating of the reaction mixture being stopped, the reaction mixture was poured into 300 ml of methanol. To this mixture, 20 ml of water was further added. Crystals which separated out in the mixture were filtered off and dried, whereby a crude product of the phthalocyanine compound No. 8 was obtained in a yield of 2.3 g.

This crude product was subjected to column chromatography (silica gel/toluene:ethyl acetate=60:1), whereby a purified phthalocyanine compound No. 8 was obtained in a yield of 1.2 g.

The analysis data of the thus obtained phthalocyanine compound No. 8 was as follows:

Solubility in 1,2-dichloroethane:

5% at room temperature

DSC analysis:

Exothermic peaks (Ti 240° C., Tp 285° C.)

TG analysis:

Reduction in weight began to be observed near 220° C.

TABLE 1 shows only the moiety of —O—CR$^1$R$^2$R$^3$ of the phthalocyanine compound of the above-mentioned formula (I), the center metal M of each of the phthalocyanine compounds Nos. 1 to 8 synthesized in Examples 1 to 8, and the maximum wavelength λmax (nm) of the absorption spectrum of each of the phthalocyanine compounds Nos. 1 to 8 when dissolved in carbon tetrachloride.

TABLE 1

| Example No. | —O—CR$^1$R$^2$R$^3$ | M | λmax (nm) |
|---|---|---|---|
| 1 | —O—CH(CF$_3$)(C$_6$H$_5$) | VO | 718 |
| 2 | —O—CH(CF$_3$)(2,4,6-trimethylphenyl) | VO | 720 |
| 3 | —O—C(CF$_3$)$_2$(C$_6$H$_5$) | VO | 711 |
| 4 | —O—C(CF$_3$)$_2$(C$_6$H$_5$) | TiO | 709 |
| 5 | —O—CH(C$_2$F$_5$)(2,4,6-trimethylphenyl) | VO | 718 |
| 6 | —O—CH(CF$_3$)(2,6-diisopropylphenyl) | VO | 719 |
| 7 | —O—CH(CF$_3$)(2,6-di-tert-butylphenyl) | VO | 719 |
| 8 | —O—CH(CF(CF$_3$)$_2$)(C$_6$H$_5$) | VO | 720 |

Application Example

A disk-shaped substrate made of polycarbonate with a diameter of 120 mm and a thickness of 1.2 mm, with guide grooves with a depth of about 1400 Å being formed on the surface of the substrate, was prepared.

The phthalocyanine compound No. 1 shown in TABLE 1 was dissolved in a mixed solvent composed of tetrahydrofuran, 2-butoxyethanol and methylcyclohexanone to prepare a coating solution.

The thus prepared coating solution was spin coated on the surface of the above prepared substrate, whereby a light absorption layer with a thickness of about 1500 Å was formed.

The maximum wavelength λmax (nm) of the absorption spectrum of the above prepared light absorption layer was 732 nm.

On the above light absorption layer, there was formed by sputtering a light reflection layer made of Au with a thickness of about 800 Å.

Furthermore, a protective layer made of an ultraviolet curing resin (Trademark "SD-17" made by Dainippon Ink & Chemicals, Incorporated) with a thickness of about 5 μm was formed on the light absorption layer, whereby a write once read many type compact disk was fabricated.

Information was recorded in this compact disk, using a commercially available CD writer (Trademark "CDE-100" made by Yamaha Corporation, 4-times speed mode), and the recorded information was reproduced to investigate the reproduction characteristics of the compact disk.

The result was that normal reproduction can be carried by this compact disk and the CI error thereof was not more than 50, which meets the CD standards which require 220 or less with respect to the CI error.

Japanese Patent Application No. 08-221699 filed Aug. 5, 1996 is hereby incorporated by reference.

What is claimed is:

1. A phthalocyanine compound of formula (1):

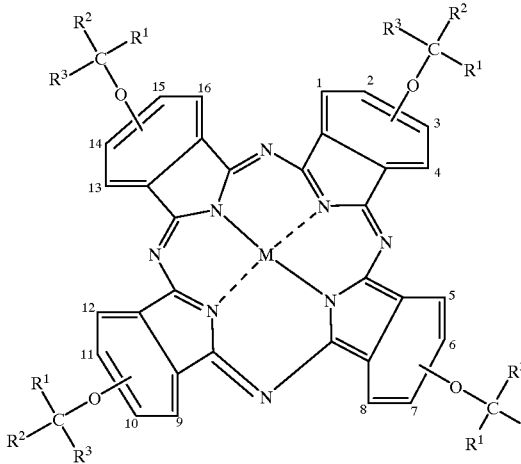

wherein numbers 1 to 16 around the phthalocyanine skeleton indicates the positions of carbon atoms, an oxygen atom is bonded to the carbon atom with position 1 or 4, to the carbon with position 5 or 8, to the carbon atom with position 9 or 12, and to the carbon atom with position 13 or 16, $R^1$ is a fluorine-atom substituted alkyl group, $R^2$ is an unsubstituted phenyl group or an alkyl-group-substituted phenyl group, $R^3$ is an unsubstituted alkyl group, a fluorine-atom substituted alkyl group or a hydrogen atom, and M represents VO or TiO.

2. The phthalocyanine compound as claimed in claim 1, wherein said fluorine-atom substituted alkyl group represented by $R^1$ is selected from the group consisting of trifluoromethyl group, pentafluroethyl group, heptafluoro-n-propyl group, heptafluoro-iso-propyl group, and nonafluoro-n-butyl group.

3. The phthalocyanine compound as claimed in claim 1, wherein said unsubstituted phenyl group or alkyl-group-substituted phenyl group represented by $R^2$ is selected from the group consisting of phenyl group, 2-methylphenyl group, 4-methyl-phenyl group, 2,5-dimethylphenyl group, 2,4-dimethyl-phenyl group, 2,4,6-trimethylphenyl group, 2,5-di-iso-propylphenyl group and 2,5-di-tert-butylphenyl group.

4. The phthalocyanine compound as claimed in claim 1, wherein said unsubstituted alkyl group represented by $R^3$ is selected from the group consisting of methyl group, ethyl group, n-propyl group, iso-propyl group, n-butyl group, iso-butyl group, sec-butyl group, tert-butyl group, and straight chain or branched pentyl group, hexyl group, heptyl group and octyl group.

5. The phthalocyanine compound as claimed in claim 1, wherein the alkyl moiety of said fluorine-atom substituted alkyl group represented by $R^3$ is selected from the group consisting of methyl group, ethyl group, n-propyl group, iso-propyl group, n-butyl group, iso-butyl group, sec-butyl group, tert-butyl group, and straight chain or branched pentyl group, hexyl group, heptyl group and octyl group.

* * * * *